US008354519B2

(12) United States Patent
Steiner et al.

(10) Patent No.: US 8,354,519 B2
(45) Date of Patent: Jan. 15, 2013

(54) CORN EVENT MIR604

(75) Inventors: Henry-York Steiner, Research Triangle Park, NC (US); Eric Chen, Research Triangle Park, NC (US); Moez Meghji, Bloomington, IL (US)

(73) Assignee: Syngenta Participations AG, Basel (CH)

( * ) Notice: Subject to any disclaimer, the term of this patent is extended or adjusted under 35 U.S.C. 154(b) by 20 days.

(21) Appl. No.: 13/009,269

(22) Filed: Jan. 19, 2011

(65) Prior Publication Data

US 2011/0111420 A1    May 12, 2011

Related U.S. Application Data

(62) Division of application No. 12/038,267, filed on Feb. 27, 2008, now Pat. No. 7,897,748, which is a division of application No. 11/059,262, filed on Feb. 16, 2005, now Pat. No. 7,361,813.

(60) Provisional application No. 60/556,260, filed on Mar. 25, 2004.

(51) Int. Cl.
*C07H 21/04* (2006.01)
*C12P 19/34* (2006.01)
*C12Q 1/68* (2006.01)
(52) U.S. Cl. .............. 536/24.33; 435/6.12; 435/91.2; 536/24.3
(58) Field of Classification Search .......... 435/6.12, 435/91.2; 536/24.33, 24.3
See application file for complete search history.

(56) References Cited

U.S. PATENT DOCUMENTS 7,241,567 B2    7/2007   Weyens et al.
2005/0216970 A1   9/2005   Steiner et al.

FOREIGN PATENT DOCUMENTS

WO         02/44407 A2      6/2002
WO      WO03/052073        6/2003

OTHER PUBLICATIONS

Okstad, et al. Genome organization is not conserved between *Bacillus cereus* and *Bacillus subtilis*. Microbiology. 1999. 145:621-631.
Okstad, et al. *B.ceieus* DNA for ORF1 ORF2 and ORF3 (2402 bp). GenBank Acc. No. Y11138. 1997.
Whitelaw, C. PUIDH43TB ZM_0.6_1.0_KB Zea mays genomic clone ZMMBTa0557G14, genomic survey sequence. GenBank Acc. No. CG066341. 2003.
Rasko, D. et al., The genome sequence of *Bacillus cereus* ATCC 10987 reveals metabolic adaptations and a large plasmid related to *Bacillus anthracis* pXO1, Nucleic Acids Res, 2004, pp. 977-988, vol. 32, No. 3.
*Schistosoma mansoni* strain Puerto Rico chromosome 2, complete genome, GenBank: HE601625, GI: 353230524.

*Primary Examiner* — Kenneth R. Horlick
*Assistant Examiner* — Joyce Tung
(74) *Attorney, Agent, or Firm* — Yoshimi D. Barron

(57) ABSTRACT

A novel transgenic corn event designated MIR604, is disclosed. The invention relates to DNA sequences of the recombinant constructs inserted into the corn genome and of genomic sequences flanking the insertion site that resulted in the MIR604 event. The invention further relates to assays for detecting the presence of the DNA sequences of MIR604, to corn plants and corn seeds comprising the genotype of MIR604 and to methods for producing a corn plant by crossing a corn plant comprising the MIR604 genotype with itself or another corn variety.

8 Claims, 2 Drawing Sheets

CORN EVENT MIR604

This application is a divisional of U.S. patent application Ser. No. 12/038,267, filed Feb. 27, 2008, now U.S. Pat. No. 7,897,748 which is a divisional of U.S. patent application Ser. No. 11/059,262, filed Feb. 16, 2005, now U.S. Pat. No. 7,361,813, which claims the benefit of priority to U.S. Provisional Application Serial No. 60/556,260, filed on Mar. 25, 2004. These documents are incorporated herein by reference in their entirety.

FIELD OF THE INVENTION

The present invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

The expression of foreign genes in plants can to be influenced by their chromosomal position, perhaps due to chromatin structure or the proximity of transcriptional regulation elements close to the integration site (See for example, Weising et al., 1988, "Foreign Genes in Plants," *Ann. Rev. Genet.* 22:421-477). Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

The present invention includes an insect resistant transgenic corn event that has incorporated into its genome a cry3A055 gene, disclosed in International Publication No. WO 03/018810, published Mar. 6, 2003, which is herein incorporated by reference, encoding a Cry3A055 insecticidal toxin, useful in controlling *Diabrotica* spp. insect pests. The transgenic corn event also has incorporated in its genome a pmi gene, encoding a phosphomannose isomerase enzyme (PMI), disclosed in U.S. Pat. No. 5,767,378, which is herein incorporated by reference, useful as a selectable marker, which allows the plant to utilize mannose as a carbon source. The present invention further includes novel isolated nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample.

SUMMARY

The present invention is drawn to a transgenic corn event, designated MIR604, comprising a novel transgenic genotype that comprises a cry3A055 gene and a pmi gene which confers insect resistance and the ability to utilize mannose as a carbon source, respectively, to the MIR604 corn event and progeny thereof. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The present invention also provides compositions and methods for detecting the presence of nucleic acids from event MIR604 based on the DNA sequence of the recombinant expression cassettes inserted into the corn genome that resulted in the MIR604 event and of genomic sequences flanking the insertion site. The MIR604 event can be further characterized by analyzing expression levels of Cry3A055 and PMI proteins as well as by testing efficacy against corn rootworm.

According to one aspect, the present invention provides an isolated nucleic acid molecule comprising at least 10 contiguous nucleotides of a heterologous DNA sequence inserted into the corn plant genome of corn event MIR604 and at least 10 contiguous nucleotides of a corn plant genome DNA flanking the point of insertion of a heterologous DNA sequence inserted into the corn plant genome of corn event MIR604. The isolated nucleic acid molecule according to this aspect may comprise at least 20 or at least 50 contiguous nucleotides of a heterologous DNA sequence inserted into the corn plant genome of corn event MIR604 and at least 20 or at least 50 contiguous nucleotides of a corn plant genome DNA flanking the point of insertion of a heterologous DNA sequence inserted into the corn plant genome of corn event MIR604.

According to another aspect, the present invention provides an isolated nucleic acid molecule comprising a nucleotide sequence that comprises at least one junction sequence of event MIR604 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the MIR604 event.

According to another aspect, the present invention provides an isolated nucleic acid linking a heterologous DNA molecule to the corn plant genome in corn event MIR604 comprising a sequence of from about 11 to about 20 contiguous nucleotides selected from the group consisting of SEQ ID NO: 1, SEQ ID NO: 2, and complements thereof.

According to another aspect, the present invention provides an isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event MIR604 are provided. Such flanking sequence primers comprise an isolated nucleic acid sequence comprising at least 10-15 contiguous nucleotides from nucleotides 1-801 as set forth in SEQ ID NO: 3 (arbitrarily designated herein as the 5' flanking sequence), or the complements thereof. In one embodiment of this aspect the flanking sequence primers are selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and complements thereof.

In another aspect of the invention, the flanking sequences primers comprise an isolated nucleic acid sequence comprising at least 10-15 contiguous nucleotides from nucleotides 507-1570 as set forth in SEQ ID NO: 4 (arbitrarily designated herein as the 3' flanking sequence), or the complements thereof. In one embodiment of this aspect the flanking sequence primers are selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 3, or SEQ ID NO: 4) and a second primer comprising a nucleotide sequence of at least 10-15 contiguous nucleotides of heterologous DNA inserted into the event MIR604 genome. The second primer preferably comprises a nucleotide sequence which is or is complementary to the insert sequence adjacent to the plant genomic flanking DNA sequence as set forth in SEQ ID NO: 3 from nucleotide position 802 through 1310 and in SEQ ID NO: 4 from nucleotide position 1 through 506.

According to another aspect of the invention, methods of detecting the presence of DNA corresponding to event MIR604 in a biological sample are provided. Such methods comprise: (a) contacting the sample comprising DNA with a pair of primers that, when used in a nucleic-acid amplification reaction with genomic DNA from corn event MIR604; produces an amplicon that is diagnostic for corn event MIR604; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, and SEQ ID NO: 4, and complements thereof.

According to another aspect, the invention provides methods of detecting the presence of a DNA corresponding to the MIR604 event in a biological sample. Such methods comprise: (a) contacting the sample comprising DNA with a probe that hybridizes under high stringency conditions with genomic DNA from corn event MIR604 and does not hybridize under high stringency conditions with DNA of a control corn plant; (b) subjecting the sample and probe to high stringency hybridization conditions; and (c) detecting hybridization of the probe to the DNA.

According to another aspect of the invention, a kit is provided for the detection of event MIR604 nucleic acids in a biological sample. The kit includes at least one DNA sequence comprising a sufficient length of polynucleotides which is or is complementary to SEQ ID NO: 1, SEQ ID NO: 2, SEQ ID NO: 3, or SEQ ID NO: 4, wherein the DNA sequences are useful as primers or probes that hybridize to isolated DNA from event MIR604, and which, upon amplification of or hybridization to a nucleic acid sequence in a sample followed by detection of the amplicon or hybridization to the target sequence, are diagnostic for the presence of nucleic acid sequences from event MIR604 in the sample. The kit further includes other materials necessary to enable nucleic acid hybridization or amplification methods.

In another aspect, the present invention provides a method of detecting corn event MIR604 protein in a biological sample comprising: (a) extracting protein from a sample of corn event MIR604 tissue; (b) assaying the extracted protein using an immunological method comprising antibody specific for the insecticidal or selectable marker protein produced by the MIR604 event; and (c) detecting the binding of said antibody to the insecticidal or selectable marker protein.

In another aspect, the present invention provides a biological sample derived from a event MIR604 corn plant, tissue, or seed, wherein the sample comprises a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the present invention provides an extract derived from a event MIR604 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided.

According to another aspect, the present invention provides a method for producing a corn plant resistant to at least corn rootworm infestation comprising: (a) sexually crossing a first parent corn plant with a second parent corn plant, wherein said first or second parent corn plant comprises corn event MIR604 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1 and SEQ ID NO: 2.

According to yet another aspect, the present invention provides a method for producing corn seed comprising crossing a first parent corn plant with a second parent corn plant and harvesting the resultant first generation corn seed, wherein the first or second parent corn plant is an inbred corn plant of the invention.

According to another aspect, the present invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

The foregoing and other aspects of the invention will become more apparent from the following detailed description.

DESCRIPTION OF THE SEQUENCES IN THE SEQUENCE LISTING

SEQ ID NO: 1 is the 5' genome-insert junction.
SEQ ID NO: 2 is the 3' insert-genome junction.
SEQ ID NO: 3 is the 5' genome+insert sequence.
SEQ ID NO: 4 is the 3' insert+genome sequence.
SEQ ID NO: 5 is corn genome flanking 5' to insert.
SEQ ID NO: 6 is corn genome flanking 3' to insert.
SEQ ID Nos: 7-15 are 5' flanking sequence primers useful in the present invention.
SEQ ID Nos: 16-20 are MTL promoter sequence primers useful in the present invention.
SEQ ID Nos: 21-28 are cry3A055 sequence primers useful in the present invention.
SEQ ID Nos: 29-30 are ZmUbiInt sequence primers useful in the present invention.
SEQ ID Nos: 31-37 are pmi sequence primers useful in the present invention.
SEQ ID NO: 38 is a NOS sequence primer useful in the present invention.
SEQ ID NO: 39-46 are 3' flanking sequence primers useful in the present invention.
SEQ ID Nos: 47-49 are cry3A055 TAQMAN primers and probe.
SEQ ID Nos: 50-52 are pmi TAQMAN primers and probe.
SEQ ID NO: 53-55 are ZmADH TAQMAN primers and probe.
SEQ ID NO: 56 is a MIR604 probe useful in the present invention.
SEQ ID NO: 57 is the sequence for the right border region.
SEQ ID NO: 58 is the sequence of the MTL promoter.
SEQ ID NO: 59 is the sequence of the cry3A055 gene.
SEQ ID NO: 60 is the sequence of the NOS terminator.
SEQ ID NO: 61 is the sequence of the ZmUbInt promoter.
SEQ ID NO: 62 is the sequence of the pmi gene.
SEQ ID NO: 63 is the sequence of the left border region.

DEFINITIONS

Figure 1:
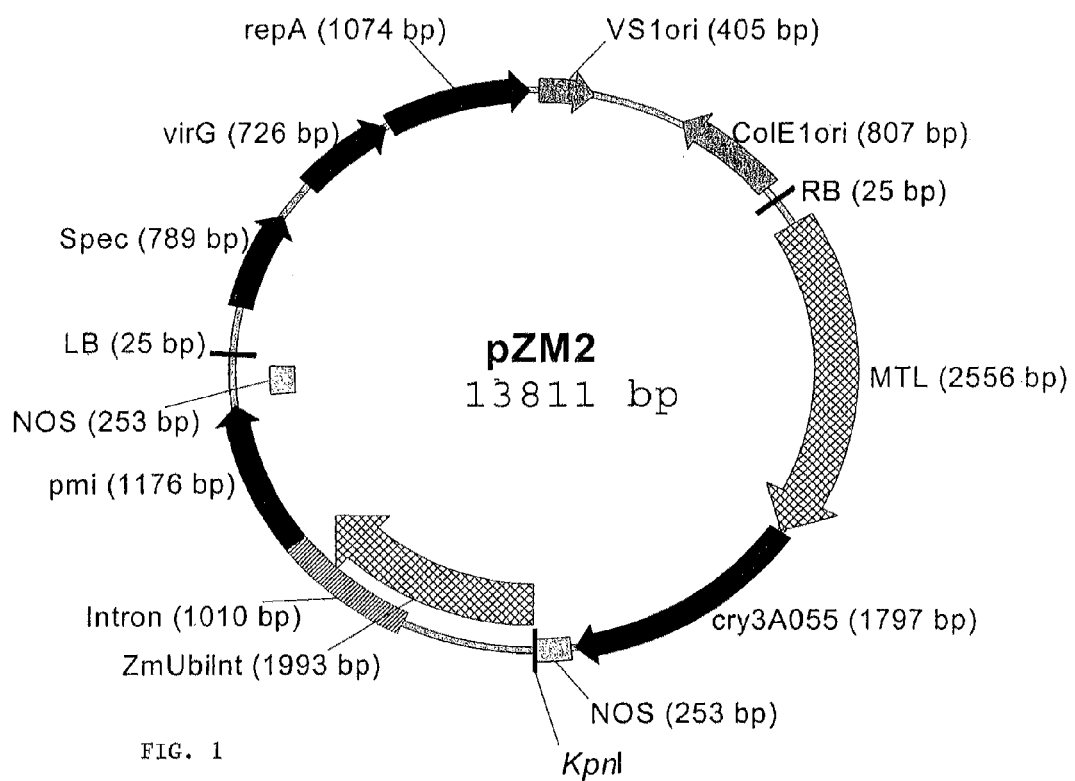
FIG. 1 illustrates a plant expression vector designated pZM26. Map identifies KpnI restriction site used for Southern analysis.
Figure 2:
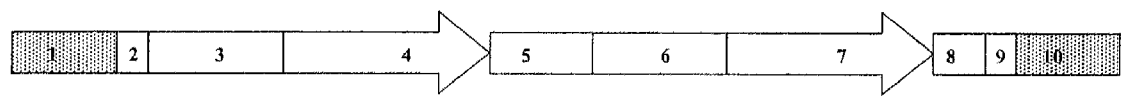
FIG. 2 is a graphical map illustrating the organization of the elements comprising the heterologous nucleic acid sequences inserted into the corn event MIR604 genome and sets forth the relative positions at which the inserted nucleic acid sequences are linked to corn genomic DNA sequences which flank the ends of the inserted heterologous DNA sequences. 1=5'flanking plant genome (SEQ ID NO: 5); 2=right border region (SEQ ID NO: 57); 3=MTL promoter (SEQ ID NO: 58); 4=cry3A055 gene (SEQ ID NO: 59); 5=NOS terminator (SEQ ID NO: 60); 6=ZmUbINT promoter (SEQ ID NO: 61); 7=pmi gene (SEQ ID NO: 62); 8=NOS terminator (SEQ ID NO: 60); 9=left border region (SEQ ID NO: 63); and 10=3' flanking plant genome (SEQ ID NO: 6).

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from MIR604 plants in a sample comprising nucleic acid probes and primers of the present invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event MIR604", "MIR604" or "MIR604 event" as used herein, means the original MIR604 transformant and/or progeny of the MIR604 transformant.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The MIR604 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the present invention, to a strand of genomic DNA from corn event, MIR604. The genomic DNA of MIR604 can be from a corn plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length, Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the present invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* (5$^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the present invention include hybridization in 7% SDS, 0.25 M NaPO$_4$ pH 7.2 at 67° C. overnight, followed by two washings in 5% SDS, 0.20 M NaPO$_4$ pH7.2 at 65° C. for 30 minutes each wash, and two washings in 1% SDS, 0.20 M NaPO$_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C. The sequences of the present invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a sequence of nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. §1.822 is used herein.

DETAILED DESCRIPTION

This invention relates to a genetically improved line of corn that produces the insect control protein, Cry3A055, and a phosphomannose isomerase enzyme (PMI) that allows the plant to utilize mannose as a carbon source. The invention is particularly drawn to a transgenic corn event designated MIR604 comprising a novel genotype, as well as to compositions and methods for detecting nucleic acids from this event in a biological sample. The invention is further drawn to corn plants comprising the MIR604 genotype, to transgenic seed from the corn plants, and to methods for producing a corn plant comprising the MIR604 genotype by crossing a corn inbred comprising the MIR604 genotype with itself or another corn line. Corn plants comprising the MIR604 genotype of the invention are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Corn plants comprising the MIR604 genotype of the invention are also able to utilize mannose as a carbon source.

In one embodiment, the present invention encompasses an isolated nucleic acid molecule comprising at least 10 or more (for example 15, 20, 25, or 50) contiguous nucleotides of a heterologous DNA sequence inserted into the corn plant genome of corn event MIR604 and at least 10 or more (for example 15, 20, 25, or 50) contiguous nucleotides of a corn plant genome DNA flanking the point of insertion of a heterologous DNA sequence inserted into the corn plant genome of corn event MIR604. Also included are nucleotide sequences that comprise 10 or more nucleotides of contiguous insert sequence from event MIR604 and at lease one nucleotide of flanking DNA from event MIR604 adjacent to the insert sequence. Such nucleotide sequences are diagnostic for event MIR604. Nucleic acid amplification of genomic DNA from the MIR604 event produces an amplicon comprising such diagnostic nucleotide sequences.

In another embodiment, the invention encompasses an isolated nucleic acid molecule comprising a nucleotide sequence which comprises at least one junction sequence of event MIR604 selected from the group consisting of SEQ ID NO: 1, SEQ ID NO: 2, and complements thereof, wherein a junction sequence spans the junction between a heterologous expression cassette inserted into the corn genome and DNA from the corn genome flanking the insertion site and is diagnostic for the event.

In another embodiment, the present invention encompasses an isolated nucleic acid linking a heterologous DNA molecule to the corn plant genome in corn event MIR604 comprising a sequence of from about 11 to about 20 contiguous nucleotides selected from the group consisting of SEQ ID NO: 1, SEQ ID NO: 2, and the complements thereof.

In another embodiment, the invention encompasses an isolated nucleic acid molecule comprising a nucleotide sequence selected from the group consisting of SEQ ID NO: 1, SEQ ID NO: 2, SEQ ID NO: 3, SEQ ID NO: 4, and complements thereof.

In one embodiment of the present invention, an amplicon comprising a nucleotide sequence selected from the group consisting of SEQ ID NO: 1, SEQ ID NO: 2, SEQ ID NO: 3, SEQ ID NO: 4, and the complements thereof is provided.

In another embodiment, the present invention encompasses flanking sequence primers for detecting event MIR604. Such flanking sequence primers comprise an isolated nucleic acid sequence comprising at least 10-15 contiguous nucleotides from nucleotides 1-801 of SEQ ID NO: 3 (arbitrarily designated herein as the 5' flanking sequence), or the complements thereof. In one aspect of this embodiment the flanking sequence primers are selected from the group consisting of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and complements thereof.

In another embodiment, the present invention encompasses flanking sequence primers that comprise at least 10-15 contiguous nucleotides from nucleotides 507-1570 of SEQ ID NO: 4 (arbitrarily designated herein as the 3' flanking sequence), or the complements thereof. In one aspect of this embodiment the flanking sequence primers are selected from the group consisting of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and complements thereof.

In still another embodiment, the present invention encompasses a pair of polynucleotide primers comprising a first polynucleotide primer and a second polynucleotide primer which function together in the presence of a corn event MIR604 DNA template in a sample to produce an amplicon diagnostic for the corn event MIR604, wherein the first primer sequence is or is complementary to a corn plant genome flanking the point of insertion of a heterologous DNA sequence inserted into the corn plant genome of corn event MIR604, and the second polynucleotide primer sequence is or is complementary to the heterologous DNA sequence inserted into the corn plant genome of the corn event MIR604.

In one aspect of this embodiment the first polynucleotide primer comprises at least 10 contiguous nucleotides from position 1-801 of SEQ ID NO: 3 or complements thereof. In a further aspect of this embodiment, the first polynucleotide primer comprises the nucleotide sequence set forth in SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or the complements thereof. In another aspect of this embodiment the first polynucleotide primer least 10 contiguous nucleotides from position 507-1570 of SEQ ID NO: 4 or complements thereof. In another aspect of this embodiment, the first polynucleotide primer comprises the nucleotide sequence set forth in SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, or the complements thereof. In yet another aspect of this embodiment, the second polynucleotide primer comprises at least 10 contiguous nucleotides of SEQ ID NO: 57, SEQ ID NO: 58, SEQ ID NO: 59, SEQ ID NO: 60, SEQ ID NO: 61, SEQ ID NO: 62, SEQ ID NO: 63, or the complements thereof. In still a further aspect of this embodiment, the second polynucleotide primer comprises the nucleotide sequence set forth in SEQ ID NO: 16 to SEQ ID NO: 38, or the complements thereof.

In another aspect of this embodiment, the first polynucleotide primer, which is set forth in SEQ ID NO: 15, and the second polynucleotide primer which is set forth in SEQ ID NO: 28, function together in the presence of a corn event MIR604 DNA template in a sample to produce an amplicon diagnostic for the corn event MIR604 as described in Example 4. In another aspect of this embodiment, the first polynucleotide primer, which is set forth in SEQ ID NO: 45, and the second polynucleotide primer which is set forth in SEQ ID NO: 27, function together in the presence of a corn event MIR604 DNA template in a sample to produce an amplicon diagnostic for the corn event MIR604 as described in Example 4.

Of course, it is well within the skill in the art to obtain additional sequence further out into the genome sequence flanking either end of the inserted heterologous DNA sequences for use as a primer sequence that can be used in such primer pairs for amplifying the sequences that are diagnostic for the MIR604 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence.

In another embodiment, the present invention encompasses a method of detecting the presence of DNA corresponding to the event MIR604 in a biological sample, wherein the method comprises: (a) contacting the sample comprising DNA with a probe that hybridizes under high stringency conditions with genomic DNA from corn event MIR604 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the present invention encompasses a method of detecting the presence of a DNA corresponding to the MIR604 event in a biological sample, wherein the method comprises: (a) contacting the sample comprising DNA with a probe that hybridizes under high stringency conditions with genomic DNA from corn event MIR604 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the MIR604 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the present invention encompasses a kit for detecting the presence of MIR604 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event MIR604, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the present invention provides for kits for detecting the presence of the target sequence, i.e., at least one of the junctions of the insert DNA with the genomic DNA of the corn plant in MIR604, in a sample containing genomic nucleic acid from MIR604. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in MIR604, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the present invention encompasses a method for detecting event MIR604 protein in a biological sample, the method comprising: (a) extracting protein from a sample of corn event MIR604 tissue; (b) assaying the extracted protein using an immunological method comprising antibody specific for the insecticidal or selectable marker protein produced by the MIR604 event; and (c) detecting the binding of said antibody to the insecticidal or selectable marker protein.

Another embodiment of the present invention encompasses a corn plant, or parts thereof, comprising the genotype of the transgenic event MIR604, wherein the genotype comprises the nucleotide sequence set forth in SEQ ID NO: 1, SEQ ID NO: 2, SEQ ID NO: 3, SEQ ID NO: 4, or the complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2166, NP2161, NP2I71, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the MIR604 genotype can be introgressed into any plant variety that can be bred with corn, including wild maize species, and thus the preferred inbred lines of this embodiment are not meant to be limiting.

In another embodiment, the present invention encompasses a corn plant comprising at least a first and a second DNA sequence linked together to form a contiguous nucleotide sequence, wherein the first DNA sequence is within a junction sequence and comprises at least about 11 contiguous nucleotides selected from the group consisting of nucleotides 792-811 of SEQ ID NO: 3; nucleotides 497-516 of SEQ ID NO: 4; SEQ ID NO: 5; SEQ ID NO: 6; and complements thereof, wherein the second DNA sequence is within the heterologous insert DNA sequence selected from the group consisting of SEQ ID NO: 57, SEQ ID NO: 58, SEQ ID NO: 59, SEQ ID NO: 60, SEQ ID NO: 61, SEQ ID NO: 62, SEQ ID NO: 63, and complements thereof; and wherein the first and the second DNA sequences are useful as nucleotide primers or probes for detecting the presence of corn event MIR604 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2.

Corn plants of the invention can be further characterized in that digesting the plant's genomic DNA with the restriction endonuclease KpnI results in a single cry3A055 hybridizing band using a cry3A055-specific probe under high stringency conditions. Exemplified herein is a cry3A055 probe comprising a nucleotide sequence set forth in SEQ ID NO: 56 or SEQ ID 59.

Corn plants of the invention can be further characterized in that digesting the plant's genomic DNA with the restriction endonuclease KpnI results in a single pmi hybridizing band using a pmi-specific probe under high stringency conditions. Exemplified herein is a pmi probe comprising a nucleotide sequence set forth in SEQ ID NO: 62.

In one embodiment, the present invention provides a corn plant, wherein the MIR604 genotype confers upon the corn plant resistance to insects or the ability to utilize mannose. In one aspect of this embodiment, the genotype conferring resistance to insects upon the corn plant comprises a cry3A055 gene. In another aspect of this embodiment, the genotype conferring upon the corn plant the ability to utilize mannose comprises a pmi gene.

In one embodiment, the present invention provides a biological sample derived from a event MIR604 corn plant, tissue, or seed, wherein the sample comprises a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one aspect of this embodiment, the sample is selected from corn flour, corn syrup, corn oil, corn starch, and cereals manufactured in whole or in part to contain corn products.

In another embodiment, the present invention provides an extract derived from a event MIR604 corn plant, tissue, or seed comprising a nucleotide sequence which is or is complementary to a nucleotide sequence selected from the group consisting of SEQ ID NO: 1 and SEQ ID NO: 2. In one aspect of this embodiment, the sequence is detected in the extract using a nucleic acid amplification or nucleic acid hybridization method. In another aspect of this embodiment, the sample is selected from corn flour, corn syrup, corn oil, cornstarch, and cereals manufactured in whole or in part to contain corn products.

In yet another embodiment, the present invention provides a method for producing a corn plant resistant to at least corn rootworm infestation comprising: (a) sexually crossing a first parent corn plant with a second parent corn plant, wherein said first or second parent corn plant comprises corn event MIR604 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1 and SEQ ID NO: 2.

In another embodiment, the present invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The present invention also encompasses the hybrid seed produced by the embodied method and hybrid plants grown from the seed.

One skilled in the art will recognize that the transgenic genotype of the present invention can be introgressed by breeding into other corn lines comprising different transgenic genotypes. For example, a corn inbred comprising the transgenic genotype of the present invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the present invention include, the glyphosate tolerant events GA21 and NK603, the glyphosate tolerant/lepidopteran insect resistant MON802 event, the lepidopteran resistant DBT418 event, the lepidopteran resistant event DAS-06275-8, the male sterile event MS3, the phosphinothricin tolerant event B16, the lepidopteran insect resistant event MON 80100, the phosphinothricin tolerant events T14 and T25, the lepidopteran insect resistant event 176, and the coleopteran resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the present invention can be treated with various seed-treatment chemicals, including insecticides, to augment or syngergize the insecticidal activity of the Cry3A055 protein. For example, the transgenic corn seed of the present invention can be treated with the commercial insecticide Cruiser®. Such a combination may used to increase the spectrum of activity and to increase the efficacy of the expressed protein and chemical.

Breeding

The transgenic genotype of the present invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, genetic marker enhanced selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by setting and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the present invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual, 3d Ed.*, Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Transformation and Selection of the MIR604 Event

The MIR604 event was produced by *Agrobacterium*-mediated transformation of the inbred corn (*Zea mays*) line A 188. Type-I embryogenic callus was transformed essentially as described in Negrotto et al. (Plant Cell Reports 19: 798-803, 2000), incorporated herein by reference, using a DNA fragment from plasmid pZM26 (FIG. 1). pZM26 contains a nucleotide sequence comprising tandem expression cassettes. The first expression cassette is comprised of a MTL promoter sequence (U.S. Pat. No. 6,018,099) operably linked to a cry3A055 coding sequence further operably linked to a nopaline synthase 3' end transcription termination and polyadenylation sequence. The second expression cassette is comprised of a maize ubiquitin promoter (ZmUbiInt) (Christensen et al. 1992 PMB 18: 675) operably linked to a pmi coding sequence further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pZM26, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the pmi and cry3A055 genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. MIR604 was chosen for further analysis based on having a single copy of the transgenes, good protein expression as identified by ELISA, and good insecticidal activity against corn rootworm.

The $T_0$ MIR604 was backcrossed to inbred corn line CG00526, creating the $T_1$ population. The $T_1$ plants were self-pollinated to create the $T_2$ generation, and this process was repeated to create a $T_3$ generation. Progeny testing of the $T_3$ plants was employed to identify homozygous (converted) families. The MIR604-converted CG00526 inbred was crossed to other elite inbred lines to create hybrids used in further studies.

Example 2

MIR604 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (adh) gene (Genbank accession no. AF044295). It will be recognized by the skilled person that other corn genes can be used as endogenous controls. Reactions were multiplexed to simultaneously amplify cry3A055 and adh or pmi and adh. For each sample, a master mixture was generated by combining 20 µL extracted genomic DNA with 35 µL 2× TAQMAN Universal PCR Master Mix (Applied Biosystems) supplemented with primers to a final concentration of 900 nM each, probes to a final concentration of 100 nM each, and water to a 70 µL final volume. This mixture was distributed into three replicates of 20 µL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event MIR604 had one copy of the cry3A055 gene and one copy of the pmi gene.

Examples of suitable primer/probe sequence combinations which were used are:

| Primer Name | Primer Sequence | SEQ ID NO: |
| --- | --- | --- |
| Cry3A055-forward | 5'-TACGAGAGCTG GGTGAACTTCA-3' | SEQ ID NO: 47 |
| Cry3A055-reverse | 5'-CGATCAGGT CCAGCACGG-3' | SEQ ID NO: 48 |

-continued

| Primer Name | Primer Sequence | SEQ ID NO: |
|---|---|---|
| Cry3A055-probe | 5'-CCGCTACCGC CGCGAGATGA-3' (5' label = FAM, 3' label = TAMRA) | SEQ ID NO: 49 |
| PMI-forward | 5'-CCGGGTGAA TCAGCGTTT-3' | SEQ ID NO: 50 |
| PMI-reverse | 5'-GCCGTGGCC TTTGACAGT-3' | SEQ ID NO: 51 |
| PMI-probe | 5'-TGCCGCCAAC GAATCACCGG-3' (5' label = FAM, 3' label = TAMRA) | SEQ ID NO: 52 |
| ZmADH-267forward | 5'-GAACGTGTGT TGGGTTTGCAT-3' | SEQ ID NO: 53 |
| ZmADH-337reverse | 5'-TCCAGCAATC CTTGCACCTT-3' | SEQ ID NO: 54 |
| ZmADH-316probe | 5'-TGCAGCCTAACC ATGCGCAGGGTA-3' (5' label = TET, 3' label = TAMRA) | SEQ ID NO: 55 |

Example 3

MIR604 Detection by Southern Blot

Genomic DNA used for southern analysis was isolated from pooled leaf tissue of ten plants representing the backcross six (BC6) generation of MIR604 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the cry3A055 gene and the pmi gene. For the negative segregant controls, DNA was isolated from pooled leaf tissue of five plants representing the BC4 generation of event MIR604. These negative segregant plants were individually analyzed using TAQMAN PCR and the assays were negative for the presence of the cry3A055 gene and the pmi gene, but were, as expected, positive for the assay internal control, the endogenous maize adh gene.

Southern analysis was carried out using conventional molecular biology techniques. Genomic DNA (7.5 µg) was digested with KpnI restriction enzyme, which has a single recognition site within the MIR604 T-DNA insert from plasmid pZM26 (FIG. 1). This approach allows for determination of the number of copies of the elements, corresponding to the specific probe used for each Southern, which have been incorporated into MIR604. This results in one hybridization band per copy of the element present in MIR604. Following agarose gel electrophoresis and alkaline transfer to a Nytran® membrane, hybridizations were carried out using element-specific full-length PCR-generated probes. The probe used in the cry3A055 and pmi Southern blots comprise the nucleotide sequences set forth in SEQ ID NO: 58 and SEQ ID NO: 61, respectively. The probes were labeled with $^{32}$P via random priming using the Rediprime™ II system (Amersham Biosciences, Cat. No. RPN1633).

The following high stringency hybridization conditions were used: 1-2 million cpm/ml are added to PerfectHyb (Sigma) supplemented with 100 µg/ml Calf Thymus DNA (Invitrogen) pre-warmed to 65° C. Pre-hybridization takes place in the same solution as above, at the same temp overnight or for at least one hour. Hybridization was carried out at 65° C. for 3 hours followed by washing 2× in 2×SSC, 0.1% SDS for 20 minutes at 65° C. and 2× in 0.1×SSC, 0.1% SDS for 20 minutes at 65° C.

Included on each Southern were three control samples: (1) DNA from a negative (non-transformed) segregant used to identify any endogenous Zea mays sequences that may cross-hybridize with the element-specific probe; (2) DNA from a negative segregant into which is introduced an amount of KpnI-digested pZM26 that is equal to one copy number based on probe length, to demonstrate the sensitivity of the experiment in detecting a single gene copy within the Zea mays genome; and (3) KpnI-digested pZM26 plasmid that is equal to one copy number based on probe length, as a positive control for hybridization as well as to demonstrate the sensitivity of the experiment.

The hybridization data provide confirmatory evidence to support the TAQMAN PCR analysis that MIR604 contains a single copy of the cry3A055 and pmi genes, and that MIR604 does not contain any of the vector backbone sequences present in pZM26. As expected for both the cry3A055 and pmi probes, the KpnI digest resulted in a single hybridization band of the correct size, demonstrating that a single copy of each gene is present in the MIR604 event. Additionally, for the backbone probe lack of hybridization demonstrates the absence of any pZM26 vector backbone sequences being incorporated into MIR604 during the transformation process.

Example 4

T-DNA Insert Sequencing

The nucleotide sequence of the entire transgene DNA insert present in event MIR604 was determined to demonstrate overall integrity of the insert, contiguousness of the functional elements and to detect any individual basepair changes. The MIR604 insert was PCR amplified from DNA derived from the BC5 generation as two individual overlapping fragments. Each fragment was amplified using one polynucleotide primer homologous to plant genomic sequences flanking the MIR604 insert and one polynucleotide primer homologous to the cry3A055 gene. To generate the 5' fragment, a first polynucleotide primer homologous to the 5' flanking sequence, 5'S1 (SEQ ID NO: 15), was combined with a second polynucleotide primer homologous to the inserted DNA within the cry3A055 gene, 5'AS1 (SEQ ID NO: 28). To generate the 3' fragment, a first polynucleotide primer homologous to the 3' flanking sequence, 9268AS (SEQ ID NO: 45), was combined with a second polynucleotide primer homologous to the inserted DNA within the cry3A055 gene, 5161S (SEQ ID NO: 27).

PCR amplification was carried out using the Expand High Fidelity PCR system (Roche, Cat. No. 1732650) and the following amplification parameters: 2 min at 94° C. for 1 cycle, followed by 10 cycles of 15 s at 94° C., 30 s at 55-65° C. and 5 min at 68° C., followed by 20 cycles of 15 s 94° C., 30 s at 55-65° C., and 5 min+5 s/cyc of 72° C., followed by 1 cycle of 7 min at 72° C.

The amplicon resulting from the PCR amplification using SEQ ID NO: 15 and SEQ ID NO: 28 comprised the 5' junction sequence (SEQ ID NO: 1). The amplicon resulting from the PCR amplification using SEQ ID NO: 45 and SEQ ID NO: 27 comprised the 3' junction sequence (SEQ ID NO: 2). Each sequencing fragment was individually cloned into the pCR®-XL-TOPO vector (Invitrogen, Cat. No. K4700-20) and three separate clones for each fragment were identified and sequenced. Sequencing was carried out using the ABI3730XL analyzer using ABI BigDye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the MIR604 insert. To further validate any individual basepair discrepancies between the MIR604 insert and the pZM26 plasmid, small (approximately 300-500 bp) PCR products specific to any regions where a basepair discrepancy was seen in the initial consensus sequence were amplified using the same methodology above. For all putative basepair discrepancies in the MIR604 insert, direct PCR product sequencing resulted in single clear peaks at all basepairs in question, indicating these discrepancies are likely present in the MIR604 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the MIR604 T-DNA insert demonstrates that the overall integrity of the insert and contiguousness of the functional elements within the insert as intended in pZM26 have been maintained. Sequence analysis revealed that some truncation occurred at the right border (RB) (SEQ ID NO: 57) and left border (LB) (SEQ ID NO: 62) ends of the T-DNA insert during the transformation process that resulted in event MIR604. The RB portion of the T-DNA insert was truncated by 44 bp and the LB end of the T-DNA insert was truncated by 43 bp. These deletions have no effect on the efficacy of the T-DNA insert and this phenomenon has been previously observed in *Agrobacterium* transformation (Tinland & Hohn, 1995. Genetic Engineering, 17: 209-229). Additionally, three base pair changes were noted in the MIR604 T-DNA insert. One discrepancy occurred within the MTL promoter, a regulatory region that does not encode a protein. The remaining two discrepancies occurred within the pmi coding sequence and did result in two amino acid changes; valine at position 61 has been substituted by alanine (V61A) and glutamine at position 210 has been substituted by histidine (Q210H). Alanine and valine are both aliphatic amino acids resulting in a conservative substitution. Replacement of glutamine with histidine results in the substitution of an acidic residue for a basic residue.

Example 5

Analysis of Flanking DNA Sequence

Corn genome DNA sequence flanking the heterologous DNA inserted into the corn plant genome of event MIR604 was obtained using OmniPlex™ Technology essentially as described in Kamberov et al (Proceedings of SPIE, *Tools for Molecular Analysis and High-Throughput Screening*, 4626: 1-12, 2002), incorporated herein by reference.

The 5' and 3' flanking sequences and junction sequences were confirmed using standard PCR procedures. The 5' flanking and junction sequences were confirmed using a first polynucleotide primer set forth in SEQ ID NO: 7, SEQ ID NO: 8, SEQ ID NO: 9, SEQ ID NO: 10, SEQ ID NO: 11, SEQ ID NO: 12 or SEQ ID NO: 13 combined with a second polynucleotide primer set forth in SEQ ID NO: 16 or SEQ ID NO: 17. The 3' flanking and junction sequences were confirmed using a first polynucleotide primer set forth in SEQ ID NO: 39, SEQ ID NO: 40, SEQ ID NO: 41, SEQ ID NO: 42, SEQ ID NO: 43 or SEQ ID NO: 44 combined with a second polynucleotide primer set forth in SEQ ID NO: 31, SEQ ID NO: 32, SEQ ID NO: 33, SEQ ID NO: 34, SEQ ID NO: 35 or SEQ ID NO: 36. It will be recognized by the skilled person that other primer sequences can be used to confirm the flanking and junction sequences.

The MIR604 insert was found to be flanked on the right boder (5' flanking sequence) by the corn genomic sequence shown in SEQ ID NO: 5 and flanked on the left border (3' flanking sequence) by the corn genomic sequence shown in SEQ ID NO: 6. The 5' junction sequence is set forth in SEQ ID NO: 1. The 3' junction sequence is set forth in SEQ ID NO: 2.

Example 6

Detection of MIR604 Protein Via ELISA

To characterize the range of expression of Cry3A055 (the active insecticidal principle) and phosphomannose isomerase (PMI) (the selectable marker) proteins in MIR604 plants, the concentrations of Cry3A055 protein and PMI were determined by ELISA in several plant tissues and whole plants at four growth stages (whorl, anthesis, seed maturity and senescence) in two hybrids (MIR604-B and MIR604-C) and one inbred (MIR604-A). The hybrids were hemizygous for the transgenes in event MIR604, whereas the inbred was homozygous for the transgenes.

Whole plants and individual parts (except pollen) were reduced to a fine powder by processing using either a coffee grinder, blender, Grindomix™ grinder (Brinkmann Instruments; Westbury, N.Y., USA), mortar with a pestle or mill, or a combination of these devices. All processing was done in the presence of either dry ice or liquid nitrogen. Samples were mixed well to ensure homogeneity. The entire plant tissue sample, or a representative sub-sample, was retained for analysis, allowing sufficient sample size for archival storage of reserve plant tissue samples. The percent dry weight of each sample was determined and the processed samples were stored at ca. −80° C. until lyophilization.

Fresh tissue (except pollen and silage) and whole-plant samples were extracted. For each sample analyzed, a 1.0 g aliquot of the powdered fresh material was weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl)benzenesulfonyl fluoride HCl, 1 mM leupeptin, pH 10], and extracted using an Autogizer® homogenizer (Tomtek; Hamden, Conn., USA). After centrifugation for 15 min at 10,000×g at 4° C., the supernatant was used for Cry3A055 and PMI analysis by ELISA. After treatment with iodoacetamide as described by Hill and Straka (1988), total protein in the extracts was quantitated using the BCA™ Protein Assay Reagent (Pierce; Rockford, Ill., USA).

Pollen extracts were prepared by suspending pollen 1:30 (w/v) in extraction buffer. After 30 min on ice, the pollen suspensions were disrupted by three passages through a French pressure cell at ca. 15,000 psi, followed by centrifugation at 14,000×g for 5 min at 4° C. Cry3A055 and PMI analyses by ELISA were performed on the supernatants as described below. Total protein was quantitated as described above.

Silage extracts were prepared by suspending silage 1:25 (w/v) in 2× extraction buffer. After 30 min on ice, the silage suspensions were extracted using a Brinkmann Polytron® Homogenizer (Brinkmann; Westbury, N.Y., USA). After centrifugation for 15 min at 10,000×g at 4° C., the supernatant was used for Cry3A055 and PMI analysis by ELISA. Total protein was quantitated as described above.

Cry3A055 Quantification

The extracts prepared as described above were quantitatively analyzed for Cry3A055 by ELISA (Tijssen, 1985) using immuno-affinity purified rabbit anti-Cry3A055 polyclonal antibodies and immuno-affinity purified goat anti-Btt (native Cry3A from *Bacillus thuringiensis* subsp. *tenebrionis*) polyclonal antibodies. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

Quantifiable levels of Cry3A055 protein were detected in all MIR604-derived plant tissues analyzed except pollen. In most cases, results are presented as means of the five replicate tissue samples. For silage, one sample was analyzed; therefore, no mean could be calculated. Control sample levels were below the limit of quantification for all stages and tissues.

Across all growth stages, mean Cry3A055 levels measured in leaves, roots and whole plants ranged from ca. 3-23 µg/g fresh wt. (4-94 µg/g dry wt.), ca. 2-14 µg/g fresh wt. (7-62 µg/g dry wt.), and about 0.9-11 µg/g fresh wt. (3-28 µg/g dry wt.), respectively. Mean Cry3A055 levels measured in kernels at seed maturity and senescence ranged from about 0.6-1.4 µg/g fresh wt. (0.8-2.0 µg/g dry wt.). Mean Cry3A055 levels measured in silk tissue at anthesis were below the lower limit of quantification (LOQ), <0.1 µg/g fresh wt. (<1.0 µg/g dry wt.). Mean Cry3A055 levels measured in silk tissue at seed maturity ranged from about 0.6-1.9 µg/g fresh wt. (1-3 µg/g dry wt.). No Cry3A055 protein was detectable in pollen from either inbred MIR604-A or hybrids MIR604-B and MIR604-C [limit of detection (LOD)=0.07 µg/g fresh wt., 0.15 µg/g dry wt.].

The levels of Cry3A055 were generally similar between hybrids for each tissue type at each time point. For the inbred line, Cry3A055 expression was generally higher than in the hybrids in leaves, roots and whole plants at whorl and anthesis stages, and in roots at seed maturity. Cry3A055 levels measured in silage tissues were on average 2.5 µg/g fresh wt. (7.3 µg/g dry wt.) over 15, 29 and 75 days. By comparison, the level of Cry3A055 measured in the chopped plant material prior to ensiling (Day 0 pre-silage) was about 8 µg/g fresh wt. (20 µg/g dry wt.).

PMI Quantification

The extracts prepared as described above were quantitatively analyzed for PMI by ELISA (Tjissen, 1985) using Protein A-purified polyclonal rabbit and immunoaffinity-purified polyclonal goat antibodies specific for PMI. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

PMI protein was detected in most of the MIR604-derived plant tissues analyzed, albeit at low levels. In most cases, results are presented as means of five replicate tissue samples. For silage, one replicate was analyzed; therefore, no mean could be calculated. Control sample levels were below the limit of quantification for all stages and tissues.

Across all plant stages, mean PMI levels measured in leaves, roots and whole plants ranged from not detectable (ND) to ca. 0.4 µg/g fresh wt. (ND-2.1 µg/g dry wt.), below the LOQ (<0.03 µg/g fresh wt.) to about 0.2 µg/g fresh wt. (<0.1-1.0 µg/g dry wt.), and below the LOQ (<0.02 µg/g fresh wt.) to about 0.3 µg/g fresh wt. (<0.04-2 µg/g dry wt.), respectively. Mean PMI levels measured in kernels at seed maturity and senescence ranged from below the LOQ (<0.06 µg/g fresh wt.) to about 0.4 µg/g fresh wt. (<0.07-0.5 µg/g dry wt.). Mean PMI levels measured in silk tissue at anthesis and seed maturity ranged from below the LOQ (<0.1 µg/g fresh wt.) to about 0.8 µg/g fresh wt. (<0.2-6.8 µg/g dry wt.). PMI in pollen ranged from about 1.9-2.6 µg/g fresh wt. (3.9-5.2 µg/g dry wt.).

The levels of PMI were generally similar among the inbred and hybrid genotypes for each tissue type at each time point. PMI was not detectable in silage at all three sampling times (day 15, 29 and 75), whereas the level measured in the chopped plant material prior to ensiling (Day 0 pre-silage) was about 0.3 µg/g fresh wt. (0.7 µg/g dry wt.).

Estimated Total Cry3A055 Protein Levels Per Acre and Per Hectare

For the inbred line (MIR604-A) and both hybrids (MIR604-B and MIR604-C), the plants reached their highest biomass at seed maturity. The plants also reached their highest estimated mean Cry3A055 levels on a per-acre (and per-hectare) basis at seed maturity and were estimated to contain about 78, 141 and 240 g Cry3A055/acre (193, 348 and 592 g/hectare) for MIR604-A, MIR604-B and MIR604-C, respectively. Over the growing season and across genotypes, estimates of Cry3A055 in MIR604-derived plants ranged from mean levels of about 8 g Cry3A055/acre (21 g Cry3A055/hectare) at senescence stage to about 240 g Cry3A055/acre (592 g Cry3A055/hectare) at seed maturity, assuming a planting density of 26,500 plants per acre (65,500 plants/hectare).

Example 7

Field Efficacy of MIR604

Western and Northern Corn Rootworm

MIR604 plants were tested for efficacy against western and northern corn rootworm at 12 locations in the United States. MIR604 was tested with and without the addition of the insecticidal seed treatment Cruiser®. Control groups consisted of seed treated with two different rates of Cruiser® and an untreated check. Treatments consisted of four replications of two 17.5-20 foot rows spaced 30" on center designed in a randomized complete block. Ten plants per treatment were chosen at random and evaluated for efficacy using a 0-3 scale wherein 0=No feeding damage (lowest rating that can be given); 1=One node (circle of roots), or the equivalent of an entire node, eaten back within approximately two inches of the stalk (soil line on the $7^{th}$ node); 2=Two complete nodes eaten; 3=Three or more nodes eaten (highest rating that can be given). Damage in between complete nodes eaten was noted as the percentage of the node missing, i.e. 1.50=1½ nodes eaten, o.25=¼ of one node eaten.

Results, shown in Table 1, demonstrate that the roots of two sibling lines of MIR604, 3-11 and 3-12, sustained significantly less feeding damage than roots from either Cruiser® treatment or the untreated control roots. MIR04-3-11 and MIR604-3-12 had root damage ratings of 0.44 and 0.42, respectively, compared to the 0.25 and 1.25 mgA/Seed Cruiser® treatments, which had damage ratings of 1.6 and 0.9, respectively, and the control line with a damage rating of 2.14. There was a trend toward lower root damage ratings in the MIR604 plants whose seed was treated with Cruiser®, suggesting that Crusier® augmented the Cry3A055 protein or that there was a possible synergy between Crusier® and Cry3A055. This was particularly evident in the 1.0 and 1.25 mgA/MIR604 seed treatments with root damage ratings of 0.33 and 0.29, respectively.

TABLE 1

Efficacy of MIR604 with and without Crusier ® seed treatment.

| Corn Line | Cruise ® Treatment (mgA/Seed) | Root Damage Rating (0-3 CRW Scale) |
| --- | --- | --- |
| MIR604-3-11 | 0 | 0.44 |
| MIR604-3-12 | 0 | 0.42 |
| MIR604 | 0.25 | 0.43 |
| MIR604 | 0.50 | 0.39 |
| MIR604 | 1.0 | 0.33 |
| MIR604 | 1.25 | 0.29 |
| Control Hybrid | 0.25 | 1.60 |
| Control Hybrid | 1.25 | 0.99 |
| Control Hybrid | 0 | 2.14 |

MIR604 efficacy was compared with commercial granular insecticide standards applied in-furrow. The experimental design was as described above. Results in Table 2 demonstrate that the efficacy of MIR604 was comparable to the commercial standards in protecting plants against corn rootworm feeding damage.

TABLE 2

Comparison of efficacy of MIR604 with commercial insecticides applied in-furrow.

| Treatment | Root Damage Rating (0-3 CRW Scale) |
| --- | --- |
| MIR604 | 0.43 |
| Force ® 3G | 0.44 |
| Aztec ® 6.7G | 0.32 |
| Lorsban ® 15 G | 0.75 |
| Untreated Check | 2.14 |

Mexican Corn Rootworm

MIR604 plants were evaluated for resistance to the Mexican corn rootworm at two locations in Texas. Experimental design was essentially the same as described above.

Results shown in Table 3 demonstrate that both MIR604 siblings sustained less feeding damage than untreated checks. There was a positive response for control of Mexican corn rootworm when Cruiser was added to the MIR604 seed. A clear rate response was evident. Results shown in Table 4 demonstrate that the efficacy of MIR604 was comparable to the commercial standards in protecting plants against Mexican corn rootworm feeding damage.

TABLE 3

Efficacy of MIR604 with and without Cruiser seed treatment against Mexican corn rootworm.

| Treatment | Cruiser ® Rate (mgA/Seed) | Root Damage Rating (0-3 CRW Scale) |
| --- | --- | --- |
| MIR604-3-11 | 0 | 1.14 |
| | 0.125 | 0.19 |
| | 0.25 | 0.18 |
| | 0.50 | 0.09 |
| | 1.25 | 0.02 |
| MIR604-3-12 | 0 | 0.68 |
| | 0.125 | 0.46 |
| | 0.25 | 0.18 |
| | 0.50 | 0.21 |
| | 1.25 | 0.04 |
| Control Hybrid | 0.125 | 1.59 |
| | 1.25 | 0.71 |
| | 0 | 2.76 |

TABLE 4

Efficacy of MIR604 compared with commercial insecticides applied in-furrow against Mexican corn rootworm.

| Treatment | Root Damage Rating (0-3 CRW Scale) |
| --- | --- |
| MIR604 | 0.68 |
| Force ® 3G | 0.66 |
| Aztec ® 6.7G | 0.88 |
| Lorsban ® 15 G | 0.81 |
| Untreated Check | 2.76 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the present invention.

What is claimed is:

1. A primer pair for detecting the presence of MIR604 nucleic acids in a biological sample, the primer pair comprising a first primer and a second primer designed to bind to a polynucleotide comprising at least 20 contiguous nucleotides of SEQ ID NO: 1 or SEQ ID NO: 2 when said polynucleotide is single stranded, wherein the first primer and the second primer, when used together in a PCR reaction, produce an amplicon that is indicative of MIR604 nucleic acids.

2. The primer pair according to claim 1, wherein the first primer is designed to bind to a MIR604 insertion sequence and the second primer is designed to bind to a flanking genomic DNA sequence downstream of the 3' end of the MIR604 insertion site or to a flanking genomic DNA sequence upstream of the 5' end of the MIR604 insertion site.

3. The primer pair according to claim 2, wherein the second primer comprises at least 10 contiguous nucleotides of nucleotides 507-1570 of SEQ ID NO: 4.

4. The primer pair according to claim 2, wherein the second primer comprises at least 10 contiguous nucleotides of nucleotides 1-801 of SEQ ID NO: 3.

5. The primer pair according to claim 2, wherein the first primer comprises a sequence selected from the group consisting of SEQ ID NOs: 27-36, and the complements thereof, and the second primer comprises a sequence selected from the group consisting of SEQ ID NOs: 39-46, and the complements thereof.

6. The primer pair according to claim 5, wherein the first primer comprises SEQ ID NO: 27 and the second primer comprises SEQ ID NO: 45.

7. The primer pair according to claim 2, wherein the first primer comprises a sequence selected from the group consisting of SEQ ID NOs: 16-28, and the complements thereof, and the second primer comprises a sequence selected from the group consisting of SEQ ID NOs: 7-15, and the complements thereof.

8. The primer pair according to claim 7, wherein the first primer comprises SEQ ID NO: 28 and the second primer comprises SEQ ID NO: 15.

* * * * *

SEQUENCE LISTING

<160> NUMBER OF SEQ ID NOS: 63

<210> SEQ ID NO 1
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: 5' genome-insert junction

<400> SEQUENCE: 1
aattcaacag aaggcgggaa                    20

<210> SEQ ID NO 2
<211> LENGTH: 20
<212> TYPE: DNA
<213> ORGANISM: Zea mays
<220> FEATURE:
<221> NAME/KEY: misc_feature
<222> LOCATION: (1)..(20)
<223> OTHER INFORMATION: 3' insert-genome junction

<400> SEQUENCE: 2
tgttattaag agttggtggt						20

<210> SEQ ID NO 3
<211> LENGTH: 1312
<212> TYPE: DNA
<213> ORGANISM: Zea mays
<220> FEATURE:
<221> NAME/KEY: misc_feature
<222> LOCATION: (1)..(1310)
<223> OTHER INFORMATION: 5' genome+insert sequence

<400> SEQUENCE: 3
ccccgcgttt cgttgcccct ggccggtacc catttggcgc cgattctttt cttgccccc     60 ggccggccgc tcgctcgcct ttggattctt ccaaagccgc tgatgggatg gtggcgaaca    120
cacccaccac ccgtctttgc ccaaagcgac ccggcacagg ccgcgccggc ttcactaacc    180
actagcgctt gtactaataa aatggtttct agcgtttgtt gctctccttt ttcttttttc    240
gccggttctt cggagccgtg tggacactgg acagcgtcca gtccagcagg catagggtgg    300
tctcggcggc ggtcgtccga cgacgatcga tctccatgag attccgcgac aggccaggac    360
ggaaagctgg gcccttctca ccaattcgcg tcggagccgg aacaagattc cctcccccaa    420
tcatttcgac gcgcccttc ttcgccaccc ctcgtggccg tgtttcgcgg ccggccctta    480
tctccttccc gtgacgcgtt cttttgtagc ttagcggccg gcacgttgct aaccaggcta    540
gcttcgttcg ttttttaatct gcctatcgag aagagaagaa aaattcgtcc atggggccac    600
ggcctcttct gcaggcattt ggcatgtgaa ggaacccgaa ccagtgaatg gagatggacg    660
gatgctgctc agatacgcag tcaaacctgc cggcgaaatt acggggggag ctggctggct    720
ggctggctgg acgccagatc acacatggat gacgcggcac ggcagctagc cgagcaggcg    780
ctctgcgcac gcaattcaac agaaggcggg aaacgacaat ctgatcatga gcggagaatt    840
aagggagtca cgttatgacc cccgccgatg acgcgggaca agccgtttta cgtttggaac    900
tgacagaacc gcaacgctgc aggaattggc cgcagcggcc atttaaatca attgggcgcg    960
ccgaattcga gctcggtaca agcttgcaca tgacaacaat tgtaagagga tggagaccac   1020
aacgatccaa caatacttct gcgacgggct gtgaagtata gagaagttaa acgcccaaaa   1080
gccattgtgt ttggaatttt tagttattct atttttcatg atgtatcttc ctctaacatg   1140
ccttaatttg caaatttggt ataactactg attgaaaata tatgtatgta aaaaaatact   1200
aagcatattt ttgaagctaa acatgatgtt atttaagaaa atatgttgtt aacagaataa   1260
gattaatatc gaaatggaaa catctgtaaa ttagaatcat cttacaagct aa            1312

<210> SEQ ID NO 4
<211> LENGTH: 1570
<212> TYPE: DNA
<213> ORGANISM: Zea mays
<220> FEATURE:
<221> NAME/KEY: misc_feature
<222> LOCATION: (1)..(1570)
<223> OTHER INFORMATION: 3' insert+genome sequence

```
<220> FEATURE:
<221> NAME/KEY: misc_feature
<222> LOCATION: (1405) and (1493)
<223> OTHER INFORMATION: n=unknown base

<400> SEQUENCE: 4
ttgtggaaag gttctcagca gttacagctt aaaccgggtg aatcagcgtt tattgccgcc      60
aacgaatcac cggtgactgt caaaggccac ggccgtttag cgcgtgttta caacaagctg     120
taagagctta ctgaaaaaat taacatctct tgctaagctg ggagctcgat ccgtcgacct     180
gcagatcgtt caaacatttg gcaataaagt ttcttaagat tgaatcctgt tgccggtctt     240
gcgatgatta tcatataatt tctgttgaat tacgttaagc atgtaataat taacatgtaa     300
tgcatgacgt tatttatgag atgggttttt atgattagag tcccgcaatt atacatttaa     360
tacgcgatag aaaacaaaat atagcgcgca aactaggata aattatcgcg cgcggtgtca     420
tctatgttac tagatctgct agccctgcag gaaatttacc ggtgcccggg cggccagcat     480
ggccgtatcc gcaatgtgtt attaagagtt ggtggtacgg gtactttaac taacgaggtg     540
tgtcgcgcag cgctcctgca cggatgtagc tttggattgc tggataatgt ctcgcgcaag     600
cgtcgtattt atttatttat ttattacagc ctccaccgcc gtgcgtgctc cgtttcggat     660
tataataaaa ctaatattaa ataaaaaaat cggattaaag gatgtttccg aaataaagat     720
ctccaccaca ggagcgaaag aaaaaaaaag agaaacgggc tatggagaaa tggtgttgcg     780
agtatacggc ggctccgtcg tcgtcggatc gacatgtaca agtaggtgc acaaaaggca     840
aagcaaaatc acctcatcaa agaccaaaag cggagcaaag aatcgatact aaatccacat     900
gtttttttg ttcctgtcta ctacgtgctg tgcctgtgcg tgaagcacga ttagtacgtg     960
tactcactct tgtcatattc ttttagtgt cttgtcacta gtcacatgga gtagcaacca    1020
tggctggcga tacccgcgat aaataaaaa aagagagagg gagtaatata ttagatactc    1080
acccattata aattataaaa tattttagag tttgaatagg tagttcttgt atatttattt    1140
atagaccttc aagtttgtcc gcctctcgag agccgaactt tgttgcccat gcttccccgg    1200
ctcaggtcat gccacctcct tcaccaaggg cacacgaag atctggtgaa gcttgtcatc    1260
accccgcgcc cttcaaacat gtgaggatgc gtcgtcgctg gcactagtag cactcattgt    1320
aggcactact ttgacagttt cctccaaata tgtagtgagg aaacacttga acaacacgtt    1380
tgggattact tatgatgttt ggttngtcca tcaatgataa ttccttcttc ttgcttaatg    1440
attggctcta gaaccgatac ttggcacatt tcatcaggaa gggcgcatgc acnaatttaa    1500
cctgttatcg atgttccggt tcctaagttg aagaaaacaa tggctaacaa ttagcccatg    1560
tgagcataac                                                          1570

<210> SEQ ID NO 5
<211> LENGTH: 801
<212> TYPE: DNA
<213> ORGANISM: Zea mays
<220> FEATURE:
<221> NAME/KEY: misc_feature
<222> LOCATION: (1)..(801)
<223> OTHER INFORMATION: 5' flanking sequence

<400> SEQUENCE: 5
ccccgcgttt cgttgcccct ggccggtacc catttggcgc cgattctttt cttgcccccc      60
ggccggccgc tcgctcgcct ttggattctt ccaaagccgc tgatgggatg gtggcgaaca     120
cacccaccac ccgtctttgc ccaaagcgac ccggcacagg ccgcgccggc ttcactaacc     180
actagcgctt gtactaataa aatggtttct agcgtttgtt gctctccttt ttcttttttc     240
```

```
gccggttctt cggagccgtg tggacactgg acagcgtcca gtccagcagg cataggggtgg    300 tctcggcggc ggtcgtccga cgacgatcga tctccatgag attccgcgac aggccaggac    360
ggaaagctgg gcccttctca ccaattcgcg tcggagccgg aacaagattc cctcccccaa    420
tcatttcgac gcgccctttc ttcgccaccc ctcgtggccg tgtttcgcgg ccggccctta    480
tctccttccc gtgacgcgtt cttttgtagc ttagcggccg gcacgttgct aaccaggcta    540
gcttcgttcg tttttaatct gcctatcgag aagagaagaa aaattcgtcc atggggccac    600
ggcctcttct gcaggcattt ggcatgtgaa ggaacccgaa ccagtgaatg gagatggacg    660
gatgctgctc agatacgcag tcaaacctgc cggcgaaatt acgggggag ctggctggct    720 ggctggctgg acgccagatc acacatggat gacgcggcac ggcagctagc cgagcaggcg    780
ctctgcgcac gcaattcaac a                                               801
```

<210> SEQ ID NO 6
<211> LENGTH: 1064
<212> TYPE: DNA
<213> ORGANISM: Zea mays
<220> FEATURE:
<221> NAME/KEY: misc_feature
<222> LOCATION: (1)..(1064)
<223> OTHER INFORMATION: 3' flanking sequence
    220>
<221> NAME/KEY: misc_feature
<222> LOCATION: (899) and (987)
<223> OTHER INFORMATION: n=unknown base

<400> SEQUENCE: 6

```
agttggtggt acgggtactt taactaacga ggtgtgtcgc gcagcgctcc tgcacggatg    60
tagctttgga ttgctggata atgtctcgcg caagcgtcgt atttatttat ttatttatta   120
cagcctccac cgccgtgcgt gctccgtttc ggattataat aaaactaata ttaaataaaa   180
aaatcggatt aaaggatgtt tccgaaataa agatctccac cacaggagcg aaagaaaaaa   240
aaagagaaac gggctatgga gaaatggtgt tgcgagtata cggcggctcc gtcgtcgtcg   300
gatcgacatg tacaaagtag gtgcacaaaa ggcaaagcaa aatcacctca tcaaagacca   360
aaagcggagc aaagaatcga tactaaatcc acatgttttt tttgttcctg tctactacgt   420
gctgtgcctg tgcgtgaagc acgattagta cgtgtactca ctcttgtcat attcttttta   480
gtgtcttgtc actagtcaca tggagtagca accatggctg gcgatacccg cgataaataa   540
aaaaaagaga gagggagtaa tatattagat actcacccat tataaattat aaaatatttt   600
agagtttgaa taggtagttc ttgtatattt atttatagac cttcaagttt gtccgcctct   660
cgagagccga actttgttgc ccatgcttcc ccggctcagg tcatgccacc tccttcacca   720
agggcacacg gaagatctgg tgaagcttgt catcaccccg cgcccttcaa acatgtgagg   780
atgcgtcgtc gctggcacta gtagcactca ttgtaggcac tactttgaca gtttcctcca   840
aatatgtagt gaggaaacac ttgaacaaca cgtttgggat tacttatgat gtttggttng   900
tccatcaatg ataattcctt cttcttgctt aatgattggc tctagaaccg atacttggca   960
catttcatca ggaagggcgc atgcacnaat ttaacctgtt atcgatgttc cggttcctaa  1020
gttgaagaaa acaatggcta acaattagcc catgtgagca taac                   1064
```

<210> SEQ ID NO 7
<211> LENGTH: 20
<212> TYPE: DNA
<213> ORGANISM: Artificial sequence
<220> FEATURE:
<223> OTHER INFORMATION: MIR604(59) primer

```
<400> SEQUENCE: 7
cgctcgcctt tggattcttc                                               20

<210> SEQ ID NO 8
<211> LENGTH: 19
<212> TYPE: DNA
<213> ORGANISM: Artificial sequence
<220> FEATURE:
<223> OTHER INFORMATION: MIR604(60) primer

<400> SEQUENCE: 8
aagccgctga tgggatggt                                                19

<210> SEQ ID NO 9
<211> LENGTH: 24
<212> TYPE: DNA
<213> ORGANISM: Artificial sequence
<220> FEATURE:
<223> OTHER INFORMATION: MIR604(54) primer

<400> SEQUENCE: 9
cgttcgtttt taatctgcct atcg                                          24

<210> SEQ ID NO 10
<211> LENGTH: 22
<212> TYPE: DNA
<213> ORGANISM: Artificial sequence
<220> FEATURE:
<223> OTHER INFORMATION: MIR604(55) primer

<400> SEQUENCE: 10
aggcatttgg catgtgaagg aa                                            22

<210> SEQ ID NO 11
<211> LENGTH: 21
<212> TYPE: DNA
<213> ORGANISM: Artificial sequence
<220> FEATURE:
<223> OTHER INFORMATION: MIR604(38) primer

<400> SEQUENCE: 11
atgtgaagga acccgaacca g                                             21

<210> SEQ ID NO 12
<211> LENGTH: 21
<212> TYPE: DNA
<213> ORGANISM: Artificial sequence
<220> FEATURE:
<223> OTHER INFORMATION: MIR604(39) primer

<400> SEQUENCE: 12
gtgaatggag atggacggat g                                             21

<210> SEQ ID NO 13
<211> LENGTH: 21
<212> TYPE: DNA
<213> ORGANISM: Artificial sequence
<220> FEATURE:
<223> OTHER INFORMATION: MIR604(51) primer

<400> SEQUENCE: 13
cagatcacac atggatgacg c                                             21

<210> SEQ ID NO 14
<211> LENGTH: 20
```

```
<212> TYPE: DNA
<213> ORGANISM: Artificial Sequence
<220> FEATURE:
<223> OTHER INFORMATION: 604 SEN primer

<400> SEQUENCE: 14
gtgacgcgtt cttttgtagc                                        20

<210> SEQ ID NO 15
<211> LENGTH: 23
<212> TYPE: DNA
<213> ORGANISM: Artificial Sequence
<220> FEATURE:
<223> OTHER INFORMATION: 5'S1 primer

<400> SEQUENCE: 15
tgaatggaga tggacggatg ctg                                    23

<210> SEQ ID NO 16
<211> LENGTH: 23
<212> TYPE: DNA
<213> ORGANISM: Artificial sequence
<220> FEATURE:
<223> OTHER INFORMATION: MTL(11) primer

<400> SEQUENCE: 16
attagaatca tcttacaagc taa                                    23

<210> SEQ ID NO 17
<211> LENGTH: 23
<212> TYPE: DNA
<213> ORGANISM: Artificial sequence
<220> FEATURE:
<223> OTHER INFORMATION: MTL(10) primer

<400> SEQUENCE: 17
ctaagagatg ttcacgcttt gag                                    23

<210> SEQ ID NO 18
<211> LENGTH: 20
<212> TYPE: DNA
<213> ORGANISM: Artificial Sequence
<220> FEATURE:
<223> OTHER INFORMATION: MTL AS  primer

<400> SEQUENCE: 18
gactcaacga aggctgctgc                                        20

<210> SEQ ID NO 19
<211> LENGTH: 20
<212> TYPE: DNA
<213> ORGANISM: Artificial Sequence
<220> FEATURE:
<223> OTHER INFORMATION: WRSEN-1 primer

<400> SEQUENCE: 19
gcatgtctct gtgtcctcgt                                        20

<210> SEQ ID NO 20
<211> LENGTH: 20
<212> TYPE: DNA
<213> ORGANISM: Artificial Sequence
<220> FEATURE:
<223> OTHER INFORMATION: WRAS-1 primer

<400> SEQUENCE: 20
aggcacgcta tcggaggtta                                        20
```

<210> SEQ ID NO 21
<211> LENGTH: 20
<212> TYPE: DNA
<213> ORGANISM: Artificial sequence
<220> FEATURE:
<223> OTHER INFORMATION: WR-1 primer

<400> SEQUENCE: 21
ggacatcgcc gagttctaca                                                  20

<210> SEQ ID NO 22
<211> LENGTH: 20
<212> TYPE: DNA
<213> ORGANISM: Artificial sequence
<220> FEATURE:
<223> OTHER INFORMATION: WR-2 primer

<400> SEQUENCE: 22
gatgtgcttc ctgatgcagg                                                  20

<210> SEQ ID NO 23
<211> LENGTH: 20
<212> TYPE: DNA
<213> ORGANISM: Artificial Sequence
<220> FEATURE:
<223> OTHER INFORMATION: WRSEN-2 primer

<400> SEQUENCE: 23
caagcaaata agacgacttg                                                  20

<210> SEQ ID NO 24
<211> LENGTH: 20
<212> TYPE: DNA
<213> ORGANISM: Artificial Sequence
<220> FEATURE:
<223> OTHER INFORMATION: WRAS-2 primer

<400> SEQUENCE: 24
agcaccacca aggacgtgat                                                  20

<210> SEQ ID NO 25
<211> LENGTH: 20
<212> TYPE: DNA
<213> ORGANISM: Artificial Sequence
<220> FEATURE:
<223> OTHER INFORMATION: WRSEN-3 primer

<400> SEQUENCE: 25
tacaacagct tcaacctggc                                                  20

<210> SEQ ID NO 26
<211> LENGTH: 20
<212> TYPE: DNA
<213> ORGANISM: Artificial Sequence
<220> FEATURE:
<223> OTHER INFORMATION: WRAS-3 primer

<400> SEQUENCE: 26
ccgtgaacta gatctgagct                                                  20

<210> SEQ ID NO 27
<211> LENGTH: 22
<212> TYPE: DNA
<213> ORGANISM: Artificial Sequence
<220> FEATURE:
<223> OTHER INFORMATION: 5161S primer

```
<400> SEQUENCE: 27
tcaaccaata ctacttcgac aa                                              22

<210> SEQ ID NO 28
<211> LENGTH: 23
<212> TYPE: DNA
<213> ORGANISM: Artificial Sequence
<220> FEATURE:
<223> OTHER INFORMATION: 5'AS1 primer

<400> SEQUENCE: 28
acaagaccat caacaagggc gac                                             23

<210> SEQ ID NO 29
<211> LENGTH: 22
<212> TYPE: DNA
<213> ORGANISM: Artificial Sequence
<220> FEATURE:
<223> OTHER INFORMATION: WRSEN-4 primer

<400> SEQUENCE: 29
atcggcgttc cggtccatgg tt                                              22

<210> SEQ ID NO 30
<211> LENGTH: 20
<212> TYPE: DNA
<213> ORGANISM: Artificial Sequence
<220> FEATURE:
<223> OTHER INFORMATION: WRAS-4 primer

<400> SEQUENCE: 30
ggaatcctgg gatggctcta                                                 20

<210> SEQ ID NO 31
<211> LENGTH: 20
<212> TYPE: DNA
<213> ORGANISM: Artificial sequence
<220> FEATURE:
<223> OTHER INFORMATION: PMI-1

<400> SEQUENCE: 31
gatgtgcttc ctgatgcagg                                                 20

<210> SEQ ID NO 32
<211> LENGTH: 18
<212> TYPE: DNA
<213> ORGANISM: Artificial sequence
<220> FEATURE:
<223> OTHER INFORMATION: PMI-2 primer

<400> SEQUENCE: 32
ctggaagtga tggcaaac                                                   18

<210> SEQ ID NO 33
<211> LENGTH: 21
<212> TYPE: DNA
<213> ORGANISM: Artificial sequence
<220> FEATURE:
<223> OTHER INFORMATION: PMI(6) primer

<400> SEQUENCE: 33
cgctgcatga ccttagtgat a                                               21

<210> SEQ ID NO 34
<211> LENGTH: 21
```

```
<212> TYPE: DNA
<213> ORGANISM: Artificial sequence
<220> FEATURE:
<223> OTHER INFORMATION: PMI(7) primer

<400> SEQUENCE: 34
cgggtgaatc agcgtttatt g                                              21

<210> SEQ ID NO 35
<211> LENGTH: 18
<212> TYPE: DNA
<213> ORGANISM: Artificial sequence
<220> FEATURE:
<223> OTHER INFORMATION: PMI(5) primer

<400> SEQUENCE: 35
ttgccgccaa cgaatcac                                                  18

<210> SEQ ID NO 36
<211> LENGTH: 23
<212> TYPE: DNA
<213> ORGANISM: Artificial sequence
<220> FEATURE:
<223> OTHER INFORMATION: PMI(16) primer

<400> SEQUENCE: 36
agtcccgcaa ttatacattt aat                                            23

<210> SEQ ID NO 37
<211> LENGTH: 20
<212> TYPE: DNA
<213> ORGANISM: Artificial Sequence
<220> FEATURE:
<223> OTHER INFORMATION: WRSEN-5 primer

<400> SEQUENCE: 37
gaaaatgccg caggtatccc                                                20

<210> SEQ ID NO 38
<211> LENGTH: 20
<212> TYPE: DNA
<213> ORGANISM: Artificial Sequence
<220> FEATURE:
<223> OTHER INFORMATION: WRAS-5 primer

<400> SEQUENCE: 38
caggtgcaca tccggcgatt                                                20

<210> SEQ ID NO 39
<211> LENGTH: 20
<212> TYPE: DNA
<213> ORGANISM: Artificial sequence
<220> FEATURE:
<223> OTHER INFORMATION: MIR604(20) primer

<400> SEQUENCE: 39
gctcctgcac ggatgtagct                                                20

<210> SEQ ID NO 40
<211> LENGTH: 23
<212> TYPE: DNA
<213> ORGANISM: Artificial sequence
<220> FEATURE:
<223> OTHER INFORMATION: MIR604(21) primer

<400> SEQUENCE: 40
gctttggatt gctggataat gtc                                            23
```

```
<210> SEQ ID NO 41
<211> LENGTH: 23
<212> TYPE: DNA
<213> ORGANISM: Artificial sequence
<220> FEATURE:
<223> OTHER INFORMATION: MIR604(31)

<400> SEQUENCE: 41
ccaccacagg agcgaaagaa aaa                                              23

<210> SEQ ID NO 42
<211> LENGTH: 22
<212> TYPE: DNA
<213> ORGANISM: Artificial sequence
<220> FEATURE:
<223> OTHER INFORMATION: MIR604(30) primer

<400> SEQUENCE: 42
gggctatgga gaaatggtgt tg                                               22

<210> SEQ ID NO 43
<211> LENGTH: 19
<212> TYPE: DNA
<213> ORGANISM: Artificial sequence
<220> FEATURE:
<223> OTHER INFORMATION: MIR604(40) primer

<400> SEQUENCE: 43
cttcaccaag ggcacacgg                                                   19

<210> SEQ ID NO 44
<211> LENGTH: 19
<212> TYPE: DNA
<213> ORGANISM: Artificial sequence
<220> FEATURE:
<223> OTHER INFORMATION: MIR604(41) primer

<400> SEQUENCE: 44
atgtgaggat gcgtcgtcg                                                   19

<210> SEQ ID NO 45
<211> LENGTH: 20
<212> TYPE: DNA
<213> ORGANISM: Artificial Sequence
<220> FEATURE:
<223> OTHER INFORMATION: 9268AS primer

<400> SEQUENCE: 45
cacggatgta gctttggatt                                                  20

<210> SEQ ID NO 46
<211> LENGTH: 20
<212> TYPE: DNA
<213> ORGANISM: Artificial Sequence
<220> FEATURE:
<223> OTHER INFORMATION: WRAS-6 primer

<400> SEQUENCE: 46
tccaccacag gagcgaaaga                                                  20

<210> SEQ ID NO 47
<211> LENGTH: 22
<212> TYPE: DNA
<213> ORGANISM: Artificial Sequence
<220> FEATURE:
<223> OTHER INFORMATION: TaqMan cry3A055-forward
```

```
<400> SEQUENCE: 47
atcgagagct gggtgaactt ca                                              22

<210> SEQ ID NO 48
<211> LENGTH: 18
<212> TYPE: DNA
<213> ORGANISM: Artificial Sequence
<220> FEATURE:
<223> OTHER INFORMATION: TaqMan cry3A055-reverse

<400> SEQUENCE: 48
cgatcaggtc cagcacgg                                                   18

<210> SEQ ID NO 49
<211> LENGTH: 20
<212> TYPE: DNA
<213> ORGANISM: Artificial Sequence
<220> FEATURE:
<223> OTHER INFORMATION: TaqMan cr3A055-probe

<400> SEQUENCE: 49
ccgctaccgc cgcgagatga                                                 20

<210> SEQ ID NO 50
<211> LENGTH: 18
<212> TYPE: DNA
<213> ORGANISM: Artificial Sequence
<220> FEATURE:
<223> OTHER INFORMATION: TaqMan pmi-forward

<400> SEQUENCE: 50
ccgggtgaat cagcgttt                                                   18

<210> SEQ ID NO 51
<211> LENGTH: 18
<212> TYPE: DNA
<213> ORGANISM: Artificial Sequence
<220> FEATURE:
<223> OTHER INFORMATION: TaqMan pmi-reverse

<400> SEQUENCE: 51
gccgtggcct ttgacagt                                                   18

<210> SEQ ID NO 52
<211> LENGTH: 20
<212> TYPE: DNA
<213> ORGANISM: Artificial Sequence
<220> FEATURE:
<223> OTHER INFORMATION: TaqMan pmi-probe

<400> SEQUENCE: 52
tgccgccaac gaatcaccgg                                                 20

<210> SEQ ID NO 53
<211> LENGTH: 21
<212> TYPE: DNA
<213> ORGANISM: Artificial Sequence
<220> FEATURE:
<223> OTHER INFORMATION: ZmADH-267 primer

<400> SEQUENCE: 53
gaacgtgtgt tgggtttgca t                                               21

<210> SEQ ID NO 54
<211> LENGTH: 20
```

```
<212> TYPE: DNA
<213> ORGANISM: Artificial Sequence
<220> FEATURE:
<223> OTHER INFORMATION: ZmADH-337 primer

<400> SEQUENCE: 54
tccagcaatc cttgcacctt                                                   20

<210> SEQ ID NO 55
<211> LENGTH: 24
<212> TYPE: DNA
<213> ORGANISM: Artificial Sequence
<220> FEATURE:
<223> OTHER INFORMATION: ZmADH-316 probe

<400> SEQUENCE: 55
tgcagcctaa ccatgcgcag ggta                                              24

<210> SEQ ID NO 56
<211> LENGTH: 779
<212> TYPE: DNA
<213> ORGANISM: Artificial sequence
<220> FEATURE:
<223> OTHER INFORMATION: MIR604 probe

<400> SEQUENCE: 56
ggacatcgcc gagttctaca agcgccagct gaagctgacc caggagtaca ccgaccactg       60
cgtgaagtgg tacaacgtgg gtctagacaa gctccgcggc agcagctacg agagctgggt      120
gaacttcaac cgctaccgcc gcgagatgac cctgaccgtg ctggacctga tcgccctgtt      180
ccccctgtac gacgtgcgcc tgtaccccaa ggaggtgaag accgagctga cccgcgacgt      240
gctgaccgac cccatcgtgg gcgtgaacaa cctgcgcggc tacggcacca ccttcagcaa      300
catcgagaac tacatccgca agccccacct gttcgactac ctgcaccgca tccagttcca      360
cacgcgtttc cagcccggct actacggcaa cgacagcttc aactactgga gcggcaacta      420
cgtgagcacc cgccccagca tcggcagcaa cgacatcatc accagcccct tctacggcaa      480
caagagcagc gagcccgtgc agaaccttga gttcaacggc gagaaggtgt accgcgccgt      540
ggctaacacc aacctggccg tgtggccctc tgcagtgtac agcggcgtga ccaaggtgga      600
gttcagccag tacaacgacc agaccgacga ggccagcacc cagacctacg acagcaagcg      660
caacgtgggc gccgtgagct gggacagcat cgaccagctg cccccgaga ccaccgacga       720 gccccctggag aagggctaca gccaccagct gaactacgtg atgtgcttcc tgatgcagg      779

<210> SEQ ID NO 57
<211> LENGTH: 183
<212> TYPE: DNA
<213> ORGANISM: Agrobacterium tumifaciens
<220> FEATURE:
<221> NAME/KEY: misc_feature
<222> LOCATION: (1)..(183)
<223> OTHER INFORMATION: Right border region

<400> SEQUENCE: 57
gaaggcggga aacgacaatc tgatcatgag cggagaatta agggagtcac gttatgaccc       60
ccgccgatga cgcgggacaa gccgttttac gtttggaact gacagaaccg caacgctgca      120
ggaattggcc gcagcggcca tttaaatcaa ttgggcgcgc cgaattcgag ctcggtacaa      180
gct                                                                    183

<210> SEQ ID NO 58
<211> LENGTH: 2556
```

```
<212> TYPE: DNA
<213> ORGANISM: Zea mays
<220> FEATURE:
<221> NAME/KEY: misc_feature
<222> LOCATION: (1)..(2556)
<223> OTHER INFORMATION: MTL promoter

<400> SEQUENCE: 58
tgcacatgac aacaattgta agaggatgga gaccacaacg atccaacaat acttctgcga      60
cgggctgtga agtatagaga agttaaacgc ccaaaagcca ttgtgtttgg aattttttagt    120 tattctatttt ttcatgatgt atcttcctct aacatgcctt aatttgcaaa tttggtataa    180
ctactgattg aaaatatatg tatgtaaaaa aatactaagc atattttga agctaaacat      240 gatgttatttt aagaaaatat gttgttaaca gaataagatt aatatcgaaa tggaaacatc    300
tgtaaattag aatcatctta caagctaaga gatgttcacg ctttgagaaa cttcttcaga    360
tcatgaccgt agaagtagct ctccaagact caacgaaggc tgctgcaatt ccacaaatgc    420
atgacatgca tccttgtaac cgtcgtcgcc gctataaaca cggataactc aattccctgc    480
tccatcaatt tagaaatgag caagcaagca cccgatcgct caccccatat gcaccaatct    540
gactcccaag ctctgtttcg cattagtacc gccagcactc cacctatagc taccaattga    600
gacctttcca gcctaagcag atcgattgat cgttagagtc aaagagttgg tggtacgggt    660
actttaacta ccatggaatg atggggcgtg atgtagagcg gaaagcgcct ccctacgcgg    720
aacaacaccc tcgccatgcc gctcgactac agcctcctcc tcgtcggcgc cacaacgagg    780
gagcccgtgg tcgcagccac cgaccagcat gtctctgtgt cctcgtccga cctcgacatg    840
tcatggcaaa cagtcggacg ccagcaccag actgacgaca tgagtctctg aagagcccgc    900
cacctagaaa gatccgagcc ctgctgctgg tagtggtaac cattttcgtc gcgctgacgc    960
ggagagcgag aggccagaaa tttatagcga ctgacgctgt ggcaggcacg ctatcggagg   1020
ttacgacgtg gcgggtcact cgacgcggag ttcacaggtc ctatccttgc atcgctcggc   1080
gcggagttta cggggactta tccttacgac gtgctctaag gttgcgataa cgggcggagg   1140
aaggcgtgtg gcgtgcggag acggtttata cacgtagtgt gcgggagtgt gtttcgtaga   1200
cgcgggaaag cacgacgact tacgaaggtt agtggaggag gaggacacac taaaatcagg   1260
acgcaagaaa ctcttctatt atagtagtag agaagagatt ataggagtgt gggttgattc   1320
taaagaaaat cgacgcagga caaccgtcaa aacgggtgct ttaatatagt agatatatat   1380
atatagagag agagagaaag tacaaaggat gcatttgtgt ctgcatatga tcggagtatt   1440
actaacggcc gtcgtaagaa ggtccatcat gcgtggagcg agcccatttg gttggttgtc   1500
aggccgcagt taaggcctcc atatatgatt gtcgtcgggc ccataacagc atctcctcca   1560
ccagtttatt gtaagaataa attaagtaga gatatttgtc gtcgggcaga agaaacttgg   1620
acaagaagaa gaagcaagct aggccaattt cttgccggca agaggaagat agtggcctct   1680
agtttatata tcggcgtgat gatgatgctc ctagctagaa atgagagaag aaaaacggac   1740
gcgtgtttgg tgtgtgtcaa tggcgtccat ccttccatca gatcagaacg atgaaaaagt   1800
caagcacggc atgcatagta tatgtatagc ttgttttagt gtggctttgc tgagacgaat   1860
gaaagcaacg gcgggcatat ttttcagtgg ctgtagcttt caggctgaaa gagacgtggc   1920
atgcaataat tcagggaatt cgtcagccaa ttgaggtagc tagtcaactt gtacattggt   1980
gcgagcaatt ttccgcactc aggagggcta gtttgagagt ccaaaaacta taggagatta   2040
aagaggctaa aatcctctcc ttatttaatt ttaaataagt agtgtatttg tattttaact   2100
cctccaaccc ttccgatttt atggctctca aactagcatt cagtctaatg catgcatgct   2160
```

| | |
|---|---|
| tggctagagg tcgtatgggg ttgttaatag catagctagc tacaagttaa ccgggtcttt | 2220 |
| tatatttaat aaggacaggc aaagtattac ttacaaataa agaataaagc taggacgaac | 2280 |
| tgctggatta ttactaaatc gaaatggacg taatattcca ggcaagaata attgttcgat | 2340 |
| caggagacaa gtggggcatt ggaccggttc ttgcaagcaa gagcctatgg cgtggtgaca | 2400 |
| cggcgcgttg cccatacatc atgcctccat cgatgatcca tcctcacttg ctataaaaag | 2460 |
| aggtgtccat ggtgctcaag ctcagccaag caaataagac gacttgtttc attgattctt | 2520 |
| caagagatcg agcttctttt gcaccacaag gtcgag | 2556 |

<210> SEQ ID NO 59
<211> LENGTH: 1797
<212> TYPE: DNA
<213> ORGANISM: Artificial Sequence
<220> FEATURE:
<223> OTHER INFORMATION: cry3A055 gene

<400> SEQUENCE: 59

| | |
|---|---|
| atgacggccg acaacaacac cgaggccctg acagcagca ccaccaagga cgtgatccag | 60 |
| aagggcatca gcgtggtggg cgacctgctg gcgtggtgg gcttcccctt cggcggcgcc | 120 |
| ctggtgagct tctacaccaa cttcctgaac accatctggc ccagcgagga ccctggaag | 180 |
| gccttcatgg agcaggtgga gggcctgatg accagaaga tcgccgacta cgccaagaac | 240 |
| aaggcactgg ccgagctaca gggcctccag aacaacgtgg aggactatgt gagcgccctg | 300 |
| agcagctggc agaagaaccc cgctgcaccg ttccgcaacc ccacagcca gggccgcatc | 360 |
| cgcgagctgt tcagccaggc cgagagccac ttccgcaaca gcatgcccag cttcgccatc | 420 |
| agcggctacg aggtgctgtt cctgaccacc tacgcccagg ccgccaacac ccacctgttc | 480 |
| ctgctgaagg acgcccaaat ctacggagag gagtggggct acgagaagga ggacatcgcc | 540 |
| gagttctaca gcgccagct gaagctgacc caggagtaca ccgaccactg cgtgaagtgg | 600 |
| tacaacgtgg gtctagacaa gctccgcggc agcagctacg agagctgggt gaacttcaac | 660 |
| cgctaccgcc gcgagatgac cctgaccgtg ctggacctga tcgccctgtt ccccctgtac | 720 |
| gacgtgcgcc tgtaccccaa ggaggtgaag accgagctga cccgcgacgt gctgaccgac | 780 |
| cccatcgtgg gcgtgaacaa cctgcgcggc tacggcacca ccttcagcaa catcgagaac | 840 |
| tacatccgca agccccacct gttcgactac ctgcaccgca tccagttcca cacgcgtttc | 900 |
| cagcccggct actacggcaa cgacagcttc aactactgga gcggcaacta cgtgagcacc | 960 |
| cgccccagca tcggcagcaa cgacatcatc accagcccct ctacggcaa caagagcagc | 1020 |
| gagcccgtgc agaaccttga gttcaacggc gagaaggtgt accgcgccgt ggctaacacc | 1080 |
| aacctggccg tgtggcccte tgcagtgtac agcggcgtga ccaaggtgga gttcagccag | 1140 |
| tacaacgacc agaccgacga ggccagcacc cagacctacg acagcaagcg caacgtgggc | 1200 |
| gccgtgagct gggacagcat cgaccagctg ccccccgaga ccaccgacga gcccctggag | 1260 |
| aagggctaca gccaccagct gaactacgtg atgtgcttcc tgatgcaggg cagccgcggc | 1320 |
| accatccccg tgctgacctg gacccacaag agcgtcgact tcttcaacat gatcgacagc | 1380 |
| aagaagatca cccagctgcc cctggtgaag gcctacaagc tccagagcgg cgccagcgtg | 1440 |
| gtggcaggcc ccgcttcac cggcggcgac atcatccagt gcaccgagaa cggcagcgcc | 1500 |
| gccaccatct acgtgacccc cgacgtgagc tacagccaga agtaccgcgc ccgcatccac | 1560 |
| tacgccagca ccagccagat caccttcacc ctgagcctgg acggggcccc cttcaaccaa | 1620 |
| tactacttcg acaagaccat caacaagggc gacacccctga cctacaacag cttcaacctg | 1680 |

| | |
|---|---|
| gccagcttca gcaccccttt cgagctgagc ggcaacaacc tccagatcgg cgtgaccggc | 1740 |
| ctgagcgccg gcgacaaggt gtacatcgac aagatcgagt tcatccccgt gaactag | 1797 |

<210> SEQ ID NO 60
<211> LENGTH: 253
<212> TYPE: DNA
<213> ORGANISM: Agrobacterium tumifaciens
<220> FEATURE:
<221> NAME/KEY: misc_feature
<222> LOCATION: (1)..(253)
<223> OTHER INFORMATION: NOS terminator

<400> SEQUENCE: 60

| | |
|---|---|
| gatcgttcaa acatttggca ataaagtttc ttaagattga atcctgttgc cggtcttgcg | 60 |
| atgattatca tataatttct gttgaattac gttaagcatg taataattaa catgtaatgc | 120 |
| atgacgttat ttatgagatg ggtttttatg attagagtcc cgcaattata catttaatac | 180 |
| gcgatagaaa acaaaatata gcgcgcaaac taggataaat tatcgcgcgc ggtgtcatct | 240 |
| atgttactag atc | 253 |

<210> SEQ ID NO 61
<211> LENGTH: 1993
<212> TYPE: DNA
<213> ORGANISM: Zea mays
<220> FEATURE:
<221> NAME/KEY: misc_feature
<222> LOCATION: (1)..(1993)
<223> OTHER INFORMATION: ZmUbInt promoter

<400> SEQUENCE: 61

| | |
|---|---|
| ctgcagtgca gcgtgacccg gtcgtgcccc tctctagaga taatgagcat tgcatgtcta | 60 |
| agttataaaa aattaccaca tattttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtatttgac aacaggactc tacagtttta tcttttagt gtgcatgtgt tctccttttt | 300 |
| ttttgcaaat agcttcacct atataatact tcatccattt tattagtaca tccatttagg | 360 |
| gtttagggtt aatggttttt atagactaat ttttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat acccttaag aaattaaaaa | 540 |
| aactaaggaa acattttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |
| acttgctccg ctgtcggcat ccagaaattg cgtggcggag cggcagacgt gagccggcac | 780 |
| ggcaggcggc ctcctcctcc tctcacggca ccggcagcta cgggggattc ctttcccacc | 840 |
| gctccttcgc tttcccttcc tcgcccgccg taataaatag acacccctc cacaccctct | 900 |
| ttccccaacc tcgtgttgtt cggagcgcac acacacacaa ccagatctcc cccaaatcca | 960 |
| cccgtcggca cctccgcttc aaggtacgcc gctcgtcctc cccccccccc cctctctacc | 1020 |
| ttctctagat cggcgttccg gtccatggtt agggcccggt agttctactt ctgttcatgt | 1080 |
| ttgtgttaga tccgtgtttg tgttagatcc gtgctgctag cgttcgtaca cggatgcgac | 1140 |
| ctgtacgtca gacacgttct gattgctaac ttgccagtgt ttctctttgg ggaatcctgg | 1200 |
| gatggctcta gccgttccgc agacgggatc gatttcatga tttttttgt ttcgttgcat | 1260 |

```
agggtttggt tgcccttttt cctttatttc aatatatgcc gtgcacttgt ttgtcgggtc    1320
atcttttcat gcttttttt gtcttggttg tgatgatgtg gtctggttgg gcggtcgttc    1380
tagatcggag tagaattctg tttcaaacta cctggtggat ttattaattt tggatctgta    1440
tgtgtgtgcc atacatattc atagttacga attgaagatg atggatggaa atatcgatct    1500
aggataggta tacatgttga tgcgggtttt actgatgcat atacagagat gcttttttgtt   1560 cgcttggttg tgatgatgtg gtgtggttgg gcggtcgttc attcgttcta gatcggagta    1620
gaatactgtt tcaaactacc tggtgtattt attaattttg gaactgtatg tgtgtgtcat    1680
acatcttcat agttacgagt ttaagatgga tggaaatatc gatctaggat aggtatacat    1740
gttgatgtgg gttttactga tgcatataca tgatggcata tgcagcatct attcatatgc    1800
tctaaccttg agtacctatc tattataata aacaagtatg ttttataatt attttgatct    1860
tgatatactt ggatgatggc atatgcagca gctatatgtg gattttttta gccctgcctt    1920
catacgctat ttatttgctt ggtactgttt cttttgtcga tgctcacccct gttgtttggt    1980 gttacttctg cag                                                       1993

<210> SEQ ID NO 62
<211> LENGTH: 1176
<212> TYPE: DNA
<213> ORGANISM: E.coli
<220> FEATURE:
<221> NAME/KEY: misc_feature
<222> LOCATION: (1)..(1176)
<223> OTHER INFORMATION: pmi gene

<400> SEQUENCE: 62
atgcaaaaac tcattaactc agtgcaaaac tatgcctggg gcagcaaaac ggcgttgact      60
gaactttatg gtatggaaaa tccgtccagc cagccgatgg ccgagctgtg gatgggcgca     120
catccgaaaa gcagttcacg agtgcagaat gccgccggag atatcgtttc actgcgtgat     180
gtgattgaga gtgataaatc gactctgctc ggagaggccg ttgccaaacg ctttggcgaa     240 ctgccttttcc tgttcaaagt attatgcgca gcacagccac tctccattca ggttcatcca     300
aacaaacaca attctgaaat cggttttgcc aaagaaaatg ccgcaggtat cccgatggat     360
gccgccgagc gtaactataa agatcctaac cacaagccgg agctggtttt tgcgctgacg     420
cctttccttg cgatgaacgc gtttcgtgaa ttttccgaga ttgtctccct actccagccg     480
gtcgcaggtg cacatccggc gattgctcac ttttttacaac agcctgatgc cgaacgttta     540
agcgaactgt tcgccagcct gttgaatatg cagggtgaag aaaaatcccg cgcgctggcg     600
attttaaaat cggcccctcga tagccagcag ggtgaaccgt ggcaaacgat tcgttaatt     660 tctgaatttt acccggaaga cagcggtctg ttctccccgc tattgctgaa tgtggtgaaa     720
ttgaaccctg cgaagcgat gttcctgttc gctgaaacac cgcacgctta cctgcaaggc     780
gtggcgctgg aagtgatggc aaactccgat aacgtgctgc gtgcgggtct gacgcctaaa     840
tacattgata ttccggaact ggttgccaat gtgaaattcg aagccaaacc ggctaaccag     900
ttgttgaccc agccggtgaa acaaggtgca gaactggact tcccgattcc agtggatgat     960
tttgccttct cgctgcatga ccttagtgat aaagaaacca ccattagcca gcagagtgcc    1020 gccatttttgt tctgcgtcga aggcgatgca acgttgtgga aggttctca gcagttacag    1080 cttaaaccgg gtgaatcagc gtttattgcc gccaacgaat caccggtgac tgtcaaaggc    1140
cacggccgtt tagcgcgtgt ttacaacaag ctgtaa                              1176
```

-continued

```
<210> SEQ ID NO 63
<211> LENGTH: 323
<212> TYPE: DNA
<213> ORGANISM: Agrobacterium tumifaciens
<220> FEATURE:
<221> NAME/KEY: misc_feature
<222> LOCATION: (1)..(323)
<223> OTHER INFORMATION: Left border region

<400> SEQUENCE: 63
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg ggtttttatg attagagtcc cgcaattata catttaatac     180
gcgatagaaa acaaaatata gcgcgcaaac taggataaat tatcgcgcgc ggtgtcatct     240
atgttactag atctgctagc cctgcaggaa atttaccggt gcccgggcgg ccagcatggc     300
cgtatccgca atgtgttatt aag                                             323
```